US007534203B2

(12) United States Patent
Gil

(10) Patent No.: US 7,534,203 B2
(45) Date of Patent: May 19, 2009

(54) VIBRATOR DEVICE WITH INFLATABLE, ALTERABLE ACCESSORIES

(75) Inventor: Noam Gil, Moshav Givton (IL)

(73) Assignee: Placeo, Herzlia (IL)

(*) Notice: Subject to any disclaimer, the term of this patent is extended or adjusted under 35 U.S.C. 154(b) by 49 days.

(21) Appl. No.: 11/671,005

(22) Filed: Feb. 5, 2007

(65) Prior Publication Data

US 2008/0188709 A1 Aug. 7, 2008

(51) Int. Cl.
*A61B 5/00* (2006.01)

(52) U.S. Cl. .......................................................... 600/38

(58) Field of Classification Search ............. 600/38–41; 128/831–845; 601/46, 68, 80, 81

See application file for complete search history.

(56) References Cited

U.S. PATENT DOCUMENTS

| | | | | |
|---|---|---|---|---|
| 4,523,584 | A * | 6/1985 | Yachia et al. | 600/38 |
| 5,344,388 | A * | 9/1994 | Maxwell et al. | 600/40 |
| 5,377,692 | A * | 1/1995 | Pfeil | 128/844 |
| 5,885,205 | A * | 3/1999 | Kassman | 600/38 |
| 6,350,230 | B1 * | 2/2002 | Kontos | 600/38 |
| 6,749,557 | B2 * | 6/2004 | Garland | 600/38 |
| 2003/0073881 | A1 * | 4/2003 | Levy | 600/38 |

* cited by examiner

*Primary Examiner*—Samuel G Gilbert
(74) *Attorney, Agent, or Firm*—Pearl Cohen Zedek Latzer, LLP

(57) ABSTRACT

Some embodiments of the present invention provide a vibrator device comprising a body, at least one accessory imbedded in said body, at least one accessory pump, and at least one tube located within the body and operatively connecting the at least one accessory to the at least one pump, wherein activation of at least one pump alters at least one aspect of at least one accessory. According to an alternative embodiment, said device may offer the same features in a sheath that fits over a conventional vibrator or a male phallus.

16 Claims, 4 Drawing Sheets

VIBRATOR DEVICE WITH INFLATABLE, ALTERABLE ACCESSORIES

FIELD OF INVENTION

This invention relates generally to vibratory devices used for sexual stimulation, and specifically to such devices that incorporate accessories whose shapes, sizes and other features may be altered.

BACKGROUND OF THE INVENTION

A sensual vibrator is an electrically driven, mechanical device designed to generate vibrations for enhancing sexual pleasure. The vibration is often generated by an electric motor with an unbalanced weight on its driveshaft, wherein the rotating weight causes vibrations when the motor is switched on.

Such vibrators are frequently battery operated. A commonly found design for commercially available vibrators is a cylindrical body with rounded distal end.

To further enhance the effects of the vibrator, a user may opt to employ one or more accessories in conjunction with that vibrator. The terms "accessory" and "accessories" refer herein to one or more objects that are affixed to or otherwise added to the body of a vibrator in order to enhance the sensation produced by that vibrator.

Vibrators currently available on the market do not normally include accessories. For those vibrators that do include accessories, the accessories usually are permanently attached to the vibrator, which eliminates the possibility of making adjustments to the size or otherwise altering the accessories. Even when the accessories may be exchanged, adjusted or otherwise altered, that alteration requires a temporary break in the use of the vibrator while the change is effected. This break in continuity may be undesirable for the user and may affect the overall efficacy to the vibrator.

SUMMARY OF THE INVENTION

Presented herein is a novel vibrator device that incorporates accessories that may be adjusted and otherwise altered, without interrupting the use of the vibrator.

According to one embodiment, the vibrator device of the present invention comprises a body, into which a plurality of accessories, at least one pump, and at least one tube are affixed. The accessories may be imbedded at various locations within the body.

The present invention provides users a choice of accessories whose aspects may be adjusted or altered. Such aspects may include, for example, size and surface texture. Additionally, the present invention enables the accessories to be adjusted all together, in groups, or individually. Furthermore, the present invention enables the accessories to be adjusted by means of a manually or electrically operated pump.

According to another embodiment of the present invention, the vibrator device comprises a sheath, into which the accessories and other components are affixed. According to such an embodiment, the vibrator device may fit onto a conventional vibrator or onto the male phallus.

The present invention also enables the user to release fluid substances such as, for example, liquids, creams, and gels, from the body of the vibrator device, by means of a manual or electrically operated fluid pump.

A key feature of the present invention is that all of these factors, namely the choice of accessories, adjustments to one or more aspects of said accessories, and the option to release substances, may be accessed and used without causing an interruption to the continuous use of the device.

BRIEF DESCRIPTION OF THE DRAWINGS

The subject matter regarded as the invention will become more clearly understood in light of the ensuing description of embodiments herein, given by way of example and for purposes of illustrative discussion of the present invention only, with reference to the accompanying drawings, wherein.

Figures 1A, 1B:
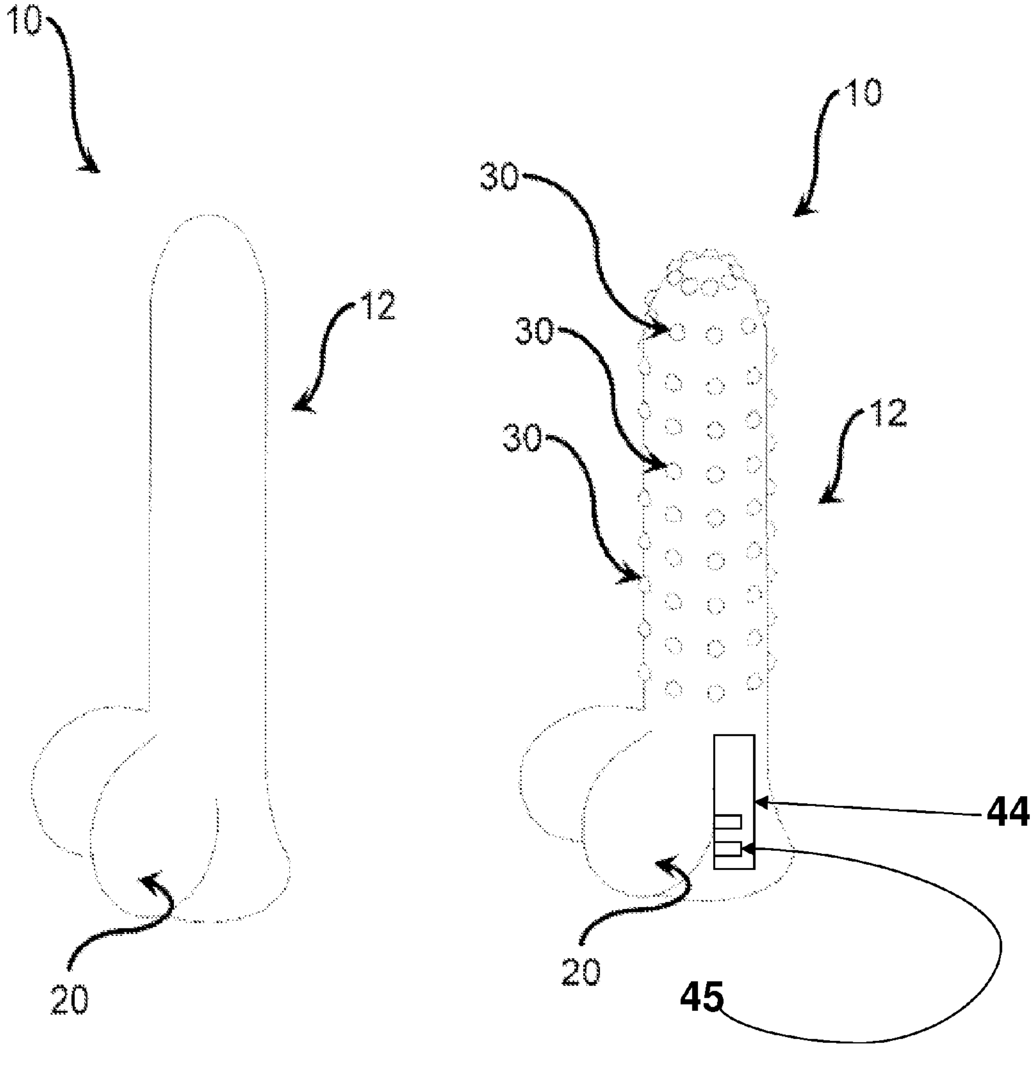
FIG. 1A is a perspective view of an embodiment of the present invention, wherein the accessories are not inflated.
FIG. 1B is a perspective view of the same embodiment, wherein the accessories are inflated.
Figure 2A:
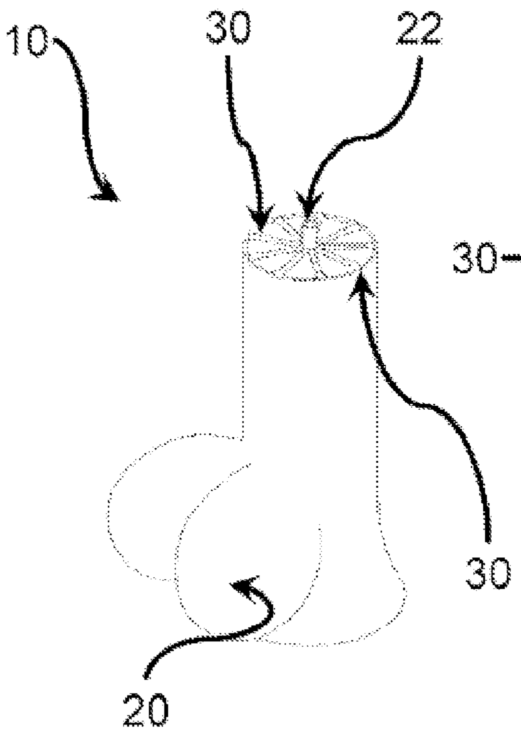
FIG. 2A is a cross-sectional, perspective view of an embodiment of the present invention, equipped with a single tube operatively connecting a plurality of accessories to a single pump, wherein the accessories are not inflated.
Figure 2B:
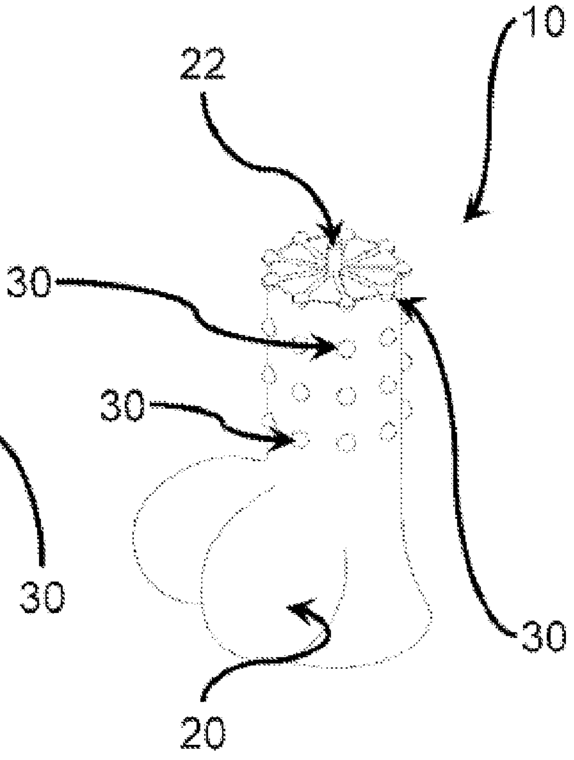
FIG. 2B is a cross-sectional, perspective view of the embodiment of FIG. 2A, wherein the accessories are inflated.

The drawings together with the description make apparent to those skilled in the art how the invention may be embodied in practice.

No attempt is made to show structural details of the invention in more detail than is necessary for a fundamental understanding of the invention.

It will be appreciated that for simplicity and clarity, of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF THE EMBODIMENTS OF THE INVENTION

Presented herein is a vibrator device 10 comprising a body 12, at least one accessory 30 imbedded in that body 12 and at least one accessory pump 20, wherein at least one tube 22 located within body 12 operatively connects at least one accessory 30 to at least one accessory pump 20. According to embodiments, the activation of at least one accessory pump 20 alters at least one aspect of at least one accessory 30. A representative embodiment of the present invention may be seen in FIGS. 1A and 1B, wherein FIG. 1A shows a vibrator device 10 whose accessories 30 are not inflated and FIG. 1B shows the same vibrator device 10 with a plurality of inflated accessories 30.

The terms "accessory" and "accessories" refer herein to one or more objects that may be affixed to or otherwise appended to the body 12 of a vibrator device 10 in order to enhance the sensation produced by that vibrator device 10

Embodiment of the present invention also enables the user to release fluid substances such as, for example, liquids, creams, and gels from vibrator device 10, as will be described in further detail below.

An embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions.

It is understood that the phraseology and terminology employed herein is not to be construed as limiting and is for descriptive purpose only.

The principles and uses of the teachings of the present invention may be better understood with reference to the accompanying description, figures and examples.

It is to be understood that the details set forth herein do not construe a limitation to an application of the invention. Furthermore, it is to be understood that the invention can be carried out or practiced in various ways and that the invention can be implemented in embodiments other than the ones outlined in the description below.

It is to be understood that the terms "including", "comprising", "consisting" and grammatical variants thereof do not preclude the addition of one or more components, features, steps, integers or groups thereof and that the terms are not to be construed as specifying components, features, steps or integers.

The phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method.

If the specification or claims refer to "an additional" element, that does not preclude there being more than one of the additional element.

It is to be understood that where the claims or specification refer to "a" or "an" element, such reference is not to be construed as there being only one of that element.

It is to be understood that where the specification states that a component feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" refers to manners, means, techniques and procedures for accomplishing a given task including, but is not limited to those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

The terms "bottom", "below", "top" and "above" as used herein do not necessarily indicate that a "bottom" component is below a "top" component, or that a component that is "below" is indeed "below" another component or that a component that is "above" is indeed "above" another component. As such, directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

According to embodiments, a vibrator device 10 of the present invention has an electric motor that is preferably battery powered, but may also be powered by other sources such as being plugged into an electric wall outlet. The electric motor of vibrator device 10 produces vibratory impulses in body 12. Body 12 has a substantially conical configuration, terminating in a substantially rounded distal end.

Vibrator device 10 may be activated by a known in the art power switch, which may be situated at the base of body 12.

According to embodiments of the present invention, accessories 30 may be imbedded into the surface of body 12 of vibrator device 10. Accessories 30 may be arranged in a regular pattern on body 12 of vibrator device 10; alternatively, accessories 30 may be placed randomly on body 12.

According to some embodiments, accessories 30 may all be substantially the same. According to other embodiments, one or more of accessories 30 may vary in one or more aspects including, inter alia, type, style, shape, size, color, texture, material, and thickness.

One or more aspects, such as size and surface texture, of accessories 30 may be adjustable according to the preferences of the user. Such adjustments enable a user of the present invention to choose accessories 30 according to, for example, the degree of friction desired, wherein the degree of friction may be determined by, for example, the rigidity or surface texture of each accessory 30. Accordingly, accessories 30 may be manufactured from different materials in order to create different effects. For example, an accessory 30 made of soft, thin material may inflate more than an accessory 30 made of a harder, thicker material.

According to some embodiments of the present invention, one or more accessories 30 may be detachable and re-attachable and additionally, the positions of two or more accessories 30 may be exchanged.

According to embodiments, a vibrator device 10 of the present invention has an electric motor 44 that is preferably battery powered 45, but may also be powered by other sources such as being plugged into an electric wall outlet. The electric motor of vibrator device 10 produces vibratory impulses in body 12. Body 12 has a substantially conical configuration, terminating in a substantially rounded distal end.

A vibrator device 10 of the present invention is equipped with at least one pneumatic accessory pump 20, situated at the base of body 12, which enables the user to inflate at least one accessory 30

Accessory pump 20 forces a gas, preferably air, into an inflatable area of each accessory 30, and inflating each accessory 30 to a different shape or size or both. This inflation may also alter other aspects of each accessories 30 such as, inter alia, surface texture. While according to some embodiments accessory pump 20 is pneumatic, other types of known in the art pumps may also be used.

According to some embodiments of the present invention, accessory pump 20 may be operated manually; according to other embodiments, accessory pump 20 may be operated electronically.

According to some embodiments of the present invention, all of accessories 30 may be inflated and deflated by a single accessory pump 20. According to some other embodiments, a single accessory pump 20 inflates and deflates a group of accessories 30, said group comprising at least one accessory 30.

According to some embodiments of the present invention, vibrator device 10 may have additional accessory pumps 20, each accessory pump 20 being connected to a portion of accessories 30. The user of the present invention may thereby choose to, for example, inflate those accessories 30 attached one pumps 20 and leave other accessories 30, for example, deflated.

According to some embodiments, a single tube 22 operatively connects one or more accessories 30 to a single accessory pump 20. Such an embodiment may be seen in FIGS. 2A, 2B, 3A and 3B. According to other embodiments, each accessory 30 may be connected to accessory pump 20 by a separate tube 22. According to yet other embodiments, a first tube 22 may operatively connect a first group of accessories 30 to accessory pump 20, a second tube 22 may operatively connect a second group of accessories 30 to accessory pump 20, and so on, wherein each group comprises one or more accessories 30.

According to yet other embodiments, wherein vibrator device 10 is equipped with more than one accessory pump 20, in addition to the above connection options, a first tube 22 may operatively connect a first group of accessories 30 to a first accessory pump 20, a second tube 22 may operatively connect a second group of accessories 30 to a second accessory pump 20, and so on, wherein each group comprises one or more accessories 30. Such an embodiment may be seen in FIGS. 4A and 4B.

By employing additional tubes 22 that lead from accessory pump 20 to accessories 30, the user is provided with a wide choice of which accessories 30 to alter, and in what combination.

Figures 3A, 3B:
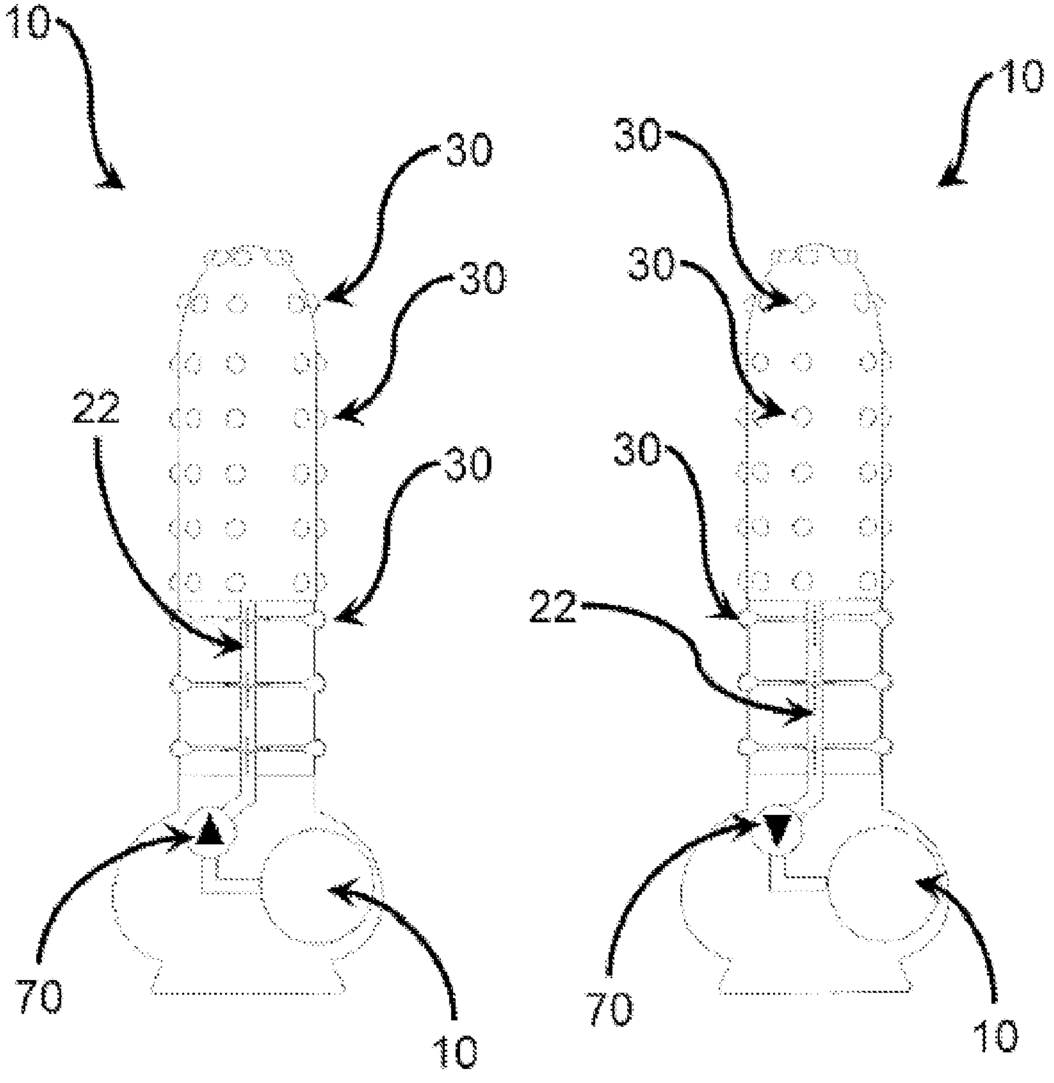
FIGS. 3A and 3B are perspective views of the embodiment of FIG. 2B, with the cover partially cut away in order to better describe the flow generated by said pump.
Figure 4A:
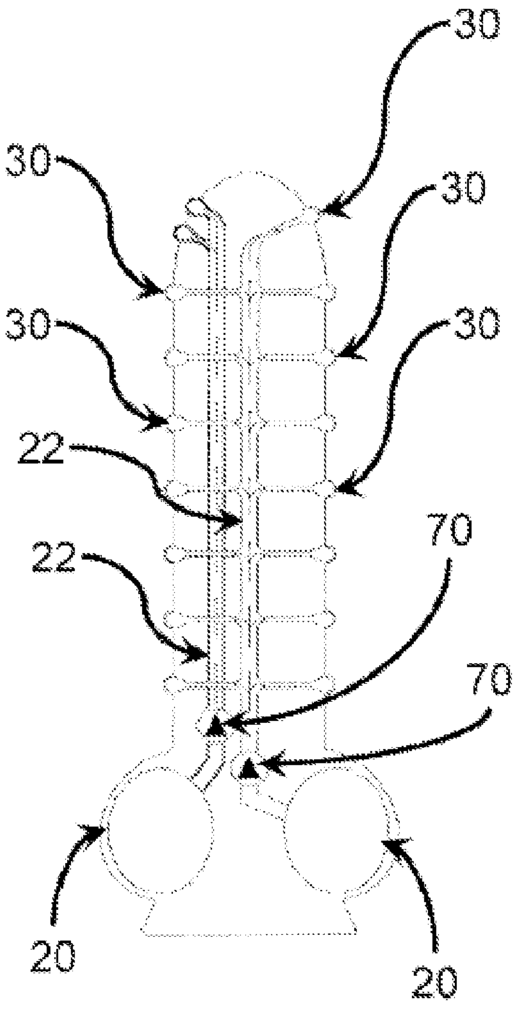
FIGS. 4A and 4B are perspective views of another embodiment of the present invention, equipped with multiple tubes operatively connecting groups of accessories to separate pumps, wherein the accessories are inflated, and with the cover partially cut away in order to better describe the ebb and flow generated by said pumps.
Figure 4B:
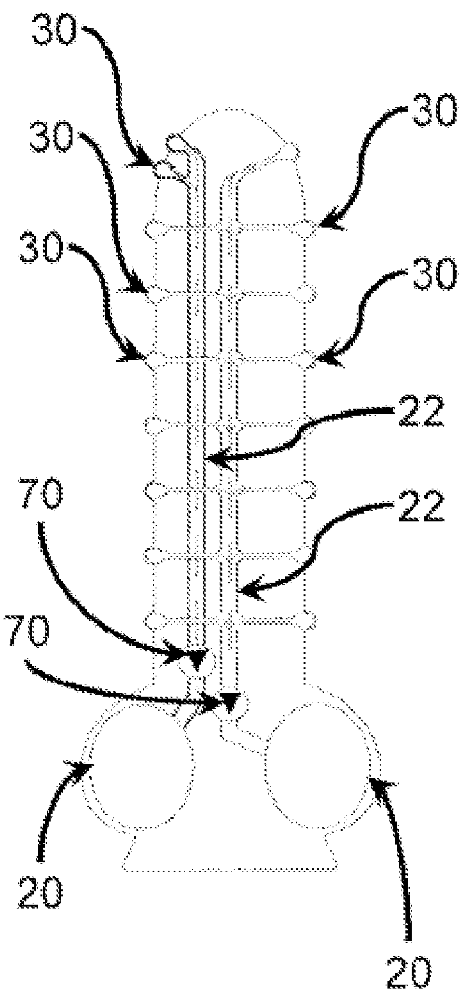

Some embodiments of the present invention are further equipped with a selector switch 70. According to such embodiments, selector switch 70 enables the user to selectively inflate and deflate one or more accessories 30 with a single accessory pump 20. Such an embodiment is described in FIGS. 3A 3B, 4A, and 4B wherein FIGS. 3A and 4A show the flow of air up into selected accessories 30 through tubes 22, and FIGS. 3B and 4B show the ebb of the air out of accessories 30. Switch system 70 may be operates manually or electronically.

According to some alternative embodiments of the present invention, vibrator device 10 comprises a sheath, at least one accessory 30, at least one accessory pump 20, and at least one tube 22 located within the sheath. Tube 22 may operatively connect accessories 30 to accessory pump 20. According to some such embodiments, one or more accessories 30 are imbedded in the sheath and activation of at least one accessory pump 20 alters the shape of at least one accessory 30, as described previously. According to such embodiments, the sheath fits over a conventional vibrator (not shown), or a male phallus (not shown).

Any of the embodiments may be further equipped with a fluid pump (not shown), situated towards the base of body 12. The fluid pump may enable releasing at least one fluid substance, including liquids, creams, gels and the like of various tastes, textures, and smells.

A channel may operatively connect the fluid pump to a reservoir and to an aperture on body 12. The channel may be located, for example, within body 12. The reservoir may hold a supply of fluid. The aperture may provide an exit point for the released fluid.

According to some embodiments, the liquids or gels may be pumped from the reservoir through at least one channel located, for example, inside vibrator device 10 and may exit the channel through at least one aperture on vibrator device 10.

According to some embodiments of the present invention, the fluid pump may be operated manually. According to some other embodiments of the present invention, the fluid pump may be operated electronically.

While the invention has been described with respect to a limited number of embodiments, these should not be construed as limitations on the scope of the invention, but rather as exemplifications of some of the embodiments. Those skilled in the art will envision other possible variations, modifications, and applications that are also within the scope of the invention. Accordingly, the scope of the invention should not be limited by what has thus far been described, but by the appended claims and their legal equivalents. Therefore, it is to be understood that alternatives, modifications, and variations of the present invention are to be construed as being within the scope and spirit of the appended claims.

What is claimed is:

1. A vibrator device comprising a body;

at least one accessory;

at least one accessory pump; and at least one tube located within the body and operatively connecting the at least one accessory to the at least one pump; wherein the at least one accessory is imbedded in the body and the activation of at least one pump alters at least one aspect of at least one accessory, wherein said accessory is detachable and re-attachable.

2. The device of claim 1, wherein the accessory pump is pneumatic.

3. The device of claim 1, further comprising a fluid pump for releasing at least one fluid substance, including liquids, creams, gels and the like, and a channel located within the body operatively connecting said pump to an aperture in said body.

4. The device of claim 1, wherein said accessory is constructed from airtight, inflatable material.

5. The device of claim 1, wherein at least one accessory has different properties including at least one of the following, size, design, material type, thickness.

6. The device of claim 1, wherein at least one material is of a different thickness.

7. The device of claim 1, wherein said accessory is inflated and deflated by a single accessory pump.

8. The device of claim 1, wherein a single accessory pump inflates and deflates one group of accessories, said group comprising at least one accessory.

9. The device of claim 1, further equipped with a selector switch, wherein said selector switch enables selective inflation and deflation of the accessories by a single accessory pump.

10. A vibrator device comprising a sheath;

at least one accessory;

at least one accessory pump; and at least one tube located within the sheath and operatively connecting the at least one accessory to the at least one pump; wherein the at least one accessory is imbedded in the sheath and the activation of at least one pump alters at least one aspect of at least one accessory, wherein said accessory is detachable and re-attachable.

11. The device of claim 10, further comprising a fluid pump for releasing least one fluid substance, including liquids, creams, gels and the like, and a channel located within the sheath operatively connecting said pump to an aperture in said sheath.

12. The device of claim 10, wherein at least one accessory has different properties including at least one of the following, size design, material type, thickness.

13. The device of claim 10, wherein at least one material is of a different thickness.

14. The device of claim 10, wherein said accessory is inflated and deflated by a single accessory pump.

15. The device of claim 10, wherein a single accessory pump inflates and deflates at least one accessory.

16. The device of claim 10, further equipped with a selector switch, wherein said selector switch enables selective inflation and deflation of the accessories by a single accessory pump.

* * * * *